United States Patent
Eustergerling et al.

(10) Patent No.: US 7,750,315 B2
(45) Date of Patent: Jul. 6, 2010

(54) APPARATUS FOR GENERATING 3D FLUORESCENCE OR LUMINESCENCE

(75) Inventors: Norbert Eustergerling, Erlangen (DE); Donal Medlar, Weisendorf (DE); Volker Pritsching, Erlangen (DE); Wolfgang Strob, Erlangen (DE)

(73) Assignee: Siemens Aktiengesellschaft (DE)

( * ) Notice: Subject to any disclaimer, the term of this patent is extended or adjusted under 35 U.S.C. 154(b) by 211 days.

(21) Appl. No.: 11/376,578

(22) Filed: Mar. 15, 2006

(65) Prior Publication Data
US 2006/0249689 A1 Nov. 9, 2006

(30) Foreign Application Priority Data
Mar. 18, 2005 (DE) .................. 10 2005 013 042

(51) Int. Cl.
*G01N 21/64* (2006.01)
(52) U.S. Cl. .................................. 250/458.1
(58) Field of Classification Search ............. 250/458.1, 250/461.1, 363.01, 362; 600/109, 178; 356/318, 356/603, 610
See application file for complete search history.

(56) References Cited

U.S. PATENT DOCUMENTS

| 4,802,759 | A | | 2/1989 | Matsumoto et al. | |
|---|---|---|---|---|---|
| 4,951,133 | A | | 8/1990 | Onoda | |
| 5,680,216 | A | * | 10/1997 | Hierholzer et al. | 356/603 |
| 6,272,368 | B1 | * | 8/2001 | Alexandrescu | 600/407 |
| 6,302,355 | B1 | * | 10/2001 | Sallee et al. | 244/3.16 |
| 6,377,700 | B1 | | 4/2002 | Mack et al. | |
| 6,456,769 | B1 | * | 9/2002 | Furusawa et al. | 385/117 |
| 6,571,119 | B2 | * | 5/2003 | Hayashi | 600/477 |
| 2001/0009269 | A1 | * | 7/2001 | Hayashi | 250/458.1 |
| 2002/0016539 | A1 | * | 2/2002 | Michaelis et al. | 600/407 |
| 2002/0045811 | A1 | * | 4/2002 | Kittrell et al. | 600/407 |
| 2003/0139661 | A1 | | 7/2003 | Kimch et al. | |

(Continued)

FOREIGN PATENT DOCUMENTS

DE 44 45 214 A1 6/1996

(Continued)

OTHER PUBLICATIONS

Novadaq Technologies Inc.: "SPY Intra-operative Imaging System", 2 pages; printed on Feb. 7, 2006 and located at http://www.novadaq.com/spy_imaging_system.php.

(Continued)

*Primary Examiner*—David P Porta
*Assistant Examiner*—Kiho Kim
(74) *Attorney, Agent, or Firm*—Brinks Hofer Gilson & Lione (57) ABSTRACT

A fluorescence or luminescence scanner and a method for generating 3D fluorescence or luminescence scans are disclosed. The scanner records a fluorescence and/or luminescence image and an optical image of the body to be examined. A pattern, such as a pattern of stripes or some other geometric pattern, is projected at a first angle onto the body to be examined. As a function of the geometric angles, based on the patterns recorded, 3D location information of each surface point of the scanned body is calculated. Both an optical image and a 3D fluorescence and/or luminescence image are obtained. The mutually superimposed (fused) images can be displayed in the form of a 3D fluorescence or luminescence scan.

15 Claims, 4 Drawing Sheets

U.S. PATENT DOCUMENTS

| | | |
|---|---|---|
| 2003/0191368 A1 | 10/2003 | Wang et al. |
| 2004/0031931 A1 | 2/2004 | Mueller et al. |
| 2004/0037390 A1* | 2/2004 | Mihara et al. ............... 378/65 |
| 2004/0037454 A1 | 2/2004 | Ozawa et al. |
| 2004/0162491 A1 | 8/2004 | Pfister et al. |
| 2004/0169854 A1 | 9/2004 | Vo-Dinh et al. |
| 2004/0249245 A1 | 12/2004 | Irion |
| 2005/0027166 A1 | 2/2005 | Matsumoto et al. |
| 2005/0068534 A1 | 3/2005 | Kleinfeld et al. |
| 2005/0073729 A1* | 4/2005 | Schmid et al. ............ 358/517 |
| 2005/0088529 A1* | 4/2005 | Geng .................... 348/207.99 |
| 2005/0148842 A1 | 7/2005 | Wang et al. |
| 2006/0195014 A1* | 8/2006 | Seibel et al. ............. 600/102 |
| 2007/0078325 A1* | 4/2007 | Fuimaono et al. ......... 600/407 |

FOREIGN PATENT DOCUMENTS

| | | |
|---|---|---|
| DE | 1999 83 341 T1 | 1/2000 |
| DE | 102 55 013 B4 | 6/2004 |
| EP | 1 374 755 A1 | 1/2004 |
| EP | 1 439 784 B1 | 2/2006 |
| EP | 1 645 841 A1 | 4/2006 |
| WO | WO 97/33157 | 9/1997 |
| WO | WO 02/41760 A2 | 5/2002 |
| WO | WO 03/105485 B1 | 12/2003 |

OTHER PUBLICATIONS

U. Mahmood et al., Near-Infrared Optical Imaging of Protease Activity for Tumor Detection; Radiology vol. 213, No. 3; pp. 866-870 and Dec. 1999.

A. Hengerer et al. "Molecular Biology for Medical Imaging," Electromedia vol. 69, No. 1; pp. 44-49; 2001.

http://www.ehendrick.org/healthy/001004.htm; printed on Feb. 7, 2006; 2 pages.

"New Multichannel Fluorescence Reflectance Imaging System for Small Animal Applications," by A. Wall et al.; European radiology, 2003, Supplement to vol. 13, p. 303.

"Multispectral Fluorescence Imager May Guide Surgical Procedure," by B.D. Butkus; Biophotonics, vol. 10, No. 4; pp. 18-19; May 2003.

Cri Products: In-Vivo Imaging, & Fluorescence Microscopy website pages; located at http://www.cri-inc.com/products/index.asp; 10 pages and printed on Dec. 22, 2005.

"Imaging Enzyme Activity and Gene expression in Vivo Through a 2.7F Catheter Feasibility Study in Mice," by M. Funovics et al.; Radiology vol. 231, No. 3; pp. 659-666 and Jun. 2004.

Xillix—Seeing Cancer in a New Light; Xillix Technologies Corp.; located at http://www.xillix.com/index_home.cfm; printed on Feb. 7, 2006 and 1 page.

DE Office Action dated Jul. 31, 2006 with an English translation.

\* cited by examiner

APPARATUS FOR GENERATING 3D FLUORESCENCE OR LUMINESCENCE

RELATED APPLICATIONS

This application claims the benefit of German Patent application DE 10 2005 013 42.9, filed on Mar. 18, 2005, which is incorporated herein by reference.

This application relates to a fluorescence or luminescence scanner and to an apparatus and a method for generating 3D fluorescence or luminescence scans.

BACKGROUND

Equipment for fluorescence or luminescence detection, hereinafter also simply called fluorescence scanners, can be used to detect various molecular factors. Substances having different molecular properties can have different fluorescent properties, which can be detected in a targeted way. The fluorescence detection is optically based and hence is noninvasive or minimally invasive. With the knowledge of the applicable fluorescent properties, it is possible to ascertain the molecular nature of a given material being examined.

Besides the fluorescent properties, luminescent properties can also be analyzed in the same way. For the sake of simplicity, the term "fluorescence" will be used exclusively hereinafter, but it should be understood to mean both fluorescence and luminescence. Moreover, still other optical emissions phenomena based on comparable excitation processes are understood to be included in this term.

In both human and veterinary medicine, molecular properties, which may be termed a "molecular signature", provide information about the state of health of a living creature or patient and can therefore be assessed diagnostically. Molecular signatures can be used in particular for detecting cancer. Still other syndromes, such as rheumatoid arthritis or arteriosclerosis of the carotid artery, can thus be identified.

Fluorescence may be excited by optical excitation. The excitation light can be in the infrared (IR) range, or in the near infrared range (NIR). The suitable optical frequency range is also dependent on the substance to be examined. Substances that themselves have no molecular or chemical properties that would be suitable for fluorescence detection can be molecularly "marked". For example, markers that with suitable preparation bind to or to be deposited only on very special molecules can be used. Such marking functions by a mechanism that, in pictorial terms, can be thought of as a lock-and-key mechanism. The marker and the molecule to be detected fit one another like a lock and key, while the marker does not bind to other substances. If the marker has known fluorescent properties then, after the binding or deposition, the marker can be optically detected. The detection of the marker then allows conclusions to be drawn as to the presence of the marked special substance. For detection, accordingly, only one detector is needed, being capable of detecting light in the wavelength that the substance in question, or the marker used, emits upon excitation.

Such fluorescence methods may be used for examinations of regions near the surface or examinations in the open body (intra-operative applications). Examples of such investigations would be detecting fluorescently marked skin cancer or the detection of tumor boundaries in the resection of fluorescently marked tumors. For example, a system for making coronary arteries and the function of bypasses (that is, the blood flow through them) visible intra-operatively has been developed.

One subject of research in biotechnology is fluorescent metabolic markers that accumulate only in certain regions (such as tumors, infections, or other foci of disease), or are distributed throughout the body but are activated only in certain regions. Activation may be by, for example, tumor-specific enzyme activities or by additional exposure to light.

In medical diagnosis, marker substances, so-called fluorophores such as indocyanin green (ICG) are known which, for example, bind to blood vessels and can be detected optically. In an imaging process, the contrast with which blood vessels are displayed can be enhanced. So-called "smart contrast agents" are also becoming increasingly important. Activatable fluorescence markers may bind, for example, to tumor tissue, and the fluorescent properties are not activated until the binding to the substance to be marked occurs. Such substances may comprise self-quenched dyes, such as Cy5.5, which are bound to larger molecules by way of specific peptides. The peptides can in turn be detected by means of specific proteases, produced for example in tumors, and can be cleaved. The fluorophores are released by the cleavage and are no longer self-quenched but instead develop their fluorescent properties. The released fluorophores can be activated for example in the near IR wavelength range of around 740 nm. One example of a marker on this basis is AF 750 (Alexa Fluor 750), with a defined absorption and emission spectrum in the wavelength range of 750 nm (excitation) and 780 nm (emission).

In medical diagnosis, such activatable markers can be used for example for intra-operative detection of tumor tissue, so that the diseased tissue can be identified exactly and then removed. One typical application is the surgical treatment of ovarian cancer. Here the diseased tissue is typically removed surgically, and the patient later treated by chemotherapy. Because of the increased sensitivity of fluorescence detection, the diseased tissue can be better detected along with various surrounding foci of disease and thus removed more completely.

In the treatment of breast cancer, typical surgical treatments are lumpectomies (or mastectomies) and lymph node sections and lymph node biopsies. Lymph nodes are typically detected optically by means of 99mTc sulfur colloids in combination with low-molecular methylene blue. The radioactive mTc sulfur colloids could be avoided by using fluorescence detection, with correspondingly favorable effects on the health of the patient.

In the removal of brain tumors, the precise demarcation of the tumor tissue, which is attainable by the use of fluorescence detection, is of obvious importance. The treatment of pancreatic tumors can benefit from additional lymph node biopsies which could be identified by fluorescence detection, to detect possible intestinal cancer. In the treatment of skin cancer, the detection of skin neoplasms could be improved by fluorescence detection. The treatment of rheumatoid arthritic diseases of joints could improve medication monitoring in the sense that the extent of protease overproduction could be detected quantitatively, and the medication provided to counteract protease overproduction could be adapted quantitatively.

In treating these diseases which are identified as examples, as well as other syndromes, an operation may be performed in which the diseased tissue is removed surgically. Fluorescence detection can be performed to improve the detection of the diseased tissue portions to be removed during an ongoing operation in the open wound. To that end, the tissue parts must be marked before the operation with a suitable substance that is then activated by binding to the diseased tissue parts. An apparatus for fluorescence detection should therefore be easy for the surgeon to manipulate and should be usable in the sterile field of the operating room.

The detection of a region marked fluorescently in this way is done by exposing the region to light in the particular excitation wavelength of the fluorescent dye, and detecting the emitted light in the corresponding emission wavelength of the fluorophore. A fluorescence scan is made by recording a fluorescence image based on fluorescent light along with an optical image based on visible light. Next, the optical image and the fluorescence image are superimposed, in order to display the fluorescence in the context of the visual image. From the superimposed view (fusion) of the optical and fluorescence images on a display device, the surgeon can detect the tumor tissue and locate it in the body of the actual patient. The fused image with the fluorescently marked tissue is displayed on a screen on the fluorescence scanner or on an external computer with image processing software.

Typically, the excitation of the fluorescence of the marker is done by means of light, and the detection device must have a light source of adequate intensity, in order to penetrate the tissue to be examined to a depth of from 0.5 to 1 cm. In addition, an optical detector is necessary that on the one hand is capable of detecting the fluorescent light and on the other, if the fluorescent light is not in the visible wavelength range, also to record an image in the visible wavelength range.

For recording both an optical image and a fluorescence image, a beam splitter may be provided. The beam splitter splits the beam of light, arriving from the object or body to be examined, into one beam whose spectrum is in the IR or near IR (NIR) range of fluorescence and a further beam in the visible wavelength range. The IR or NIR beam is carried to an image sensor, provided specifically for it, and the visible beam is carried to an image sensor suitable for it. The two image sensors, separately from one another, simultaneously record an image. Thus, the fluorescence image and the optical image are available and can be superimposed on one another. It is a disadvantage that two image sensors are required, and that the construction is relatively bulky.

For recording both an optical image and a fluorescence image, a filter changer can be located in the beam path prior to the image sensor. The filter changer changes to a specific filter for taking fluorescence images and a specific filter for taking optical images. At least for recording fluorescence images, a change must be made to a filter that filters out light in the visible wavelength range, because otherwise the fluorescent light would be washed out by the visible light. A disadvantage is that the filter changer is mechanically complicated and makes for a bulky construction. In addition, the optical and the fluorescence image must be taken in succession, which makes the recording more time-consuming and tends to promote artifacts in the image caused by scanner motion between obtaining the images.

Existing apparatus for generating fluorescence scans is predominantly limited to the generation of 2D scans. It can be desirable to have 3D scans available as well. 3D information may be acquired by time-domain measuring methods, spectroscopically by laser projection, or by means of fluorescence mediated tomography. The known methods are complicated, however, because they are partly based on using still measuring methods that are highly computation-intensive.

SUMMARY

An apparatus for recording both an optical image and a fluorescence image is disclosed, including an image sensor which has a filter layer with at least two different surface portions with different optical filtering properties. At least one surface portion admits fluorescent light and filters out at least visible light, and at least one further surface portion admits visible light. Such an image sensor can record an optical and a fluorescence image simultaneously. The image sensor may for example be embodied as a CCD camera and the image detector as a CCD chip, but other picture-taking technologies can also be used.

The body to be examined is exposed to light at a wavelength that is in the wavelength range of the excitation spectrum of the particular fluorescence marker, and the emitted fluorescence image is subjected to suitable optical filtration and recorded with an image detector. A pattern, such as a striped pattern or other geometrical pattern, is then projected onto the body to be examined, and an image of the pattern is made. The pattern projection beam and the connecting line between the body to be examined and the image detector form a defined angle. From the defined, known, angle and the distorted pattern that is visible on the body to be examined, the 3D location information of each surface point of the body may be calculated. This calculation of the 3D location information is based on measuring methods and on geometric bases for calculation. Consequently, both an optical image and a 3D fluorescence image are obtained, which can be displayed superimposed (fused) as a 3D fluorescence scan.

The recording of the fluorescence image and the recording of a pattern as well as the ensuing calculation of the 3D location information may be repeated multiple times from different angles of observation, or in other words at different angles relative to the body to be examined. As a result, optical 3D fluorescence scans may be obtained of a relatively large region of the body, or even the entire body.

For the incremental generation of a plurality of 3D fluorescence scans from different angles of observation, the fluorescence scanner may be rotated incrementally about at least one axis around the body to be examined. As a result, 3D fluorescence scans of a relatively large body region are obtained without the body to be examined itself having to be rotated. Avoiding rotation or motion of the body to be examined may be especially desirable in surgical situations.

In another aspect, in the incremental generation of a plurality of 3D fluorescence scans from different angles of observation, the body to be examined is rotated in increments about at least one axis. As a result, a positioning device that may be present for another purpose can be used for rotating and moving the body to be examined.

DETAILED DESCRIPTION

Exemplary embodiments may be better understood with reference to the drawings, but these embodiments are not intended to be of a limiting nature. Like numbered elements in the same or different drawings perform equivalent functions.

A fluorescence or luminescence scanner and an apparatus and a method for generating 3D fluorescence or luminescence scans are provided. The fluorescence or luminescence scanner records a fluorescence and/or luminescence image and an optical image of the body to be examined. A pattern, such as a pattern of stripes or some other geometric pattern, is projected at a first geometric angle onto the body to be examined. The projection pattern is recorded at a second geometric angle that differs from the first. As a function of the geometric angles, based on the pattern recorded, 3D location information of each surface point of the scanned body is calculated. Both an optical image and a 3D fluorescence and/or luminescence image are obtained. The mutually superimposed (fused) images can be displayed in the form of a 3D fluorescence or luminescence scan. In addition, to obtain a 3D fluorescence or luminescence scan of the entire body, a series of individual 3D fluorescence or luminescence scans can be recorded.

Figure 1:
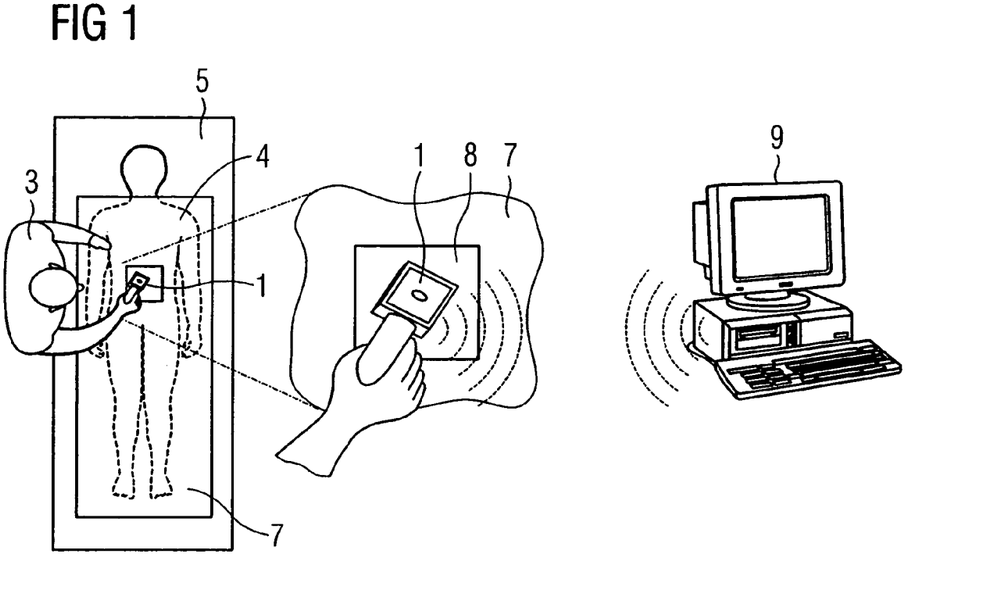
FIG. 1 is an application scenario for a fluorescence scanner in one embodiment.

FIG. 1 schematically illustrates a scenario for using a fluorescence scanner 1. A body 4 to be examined, which may covered by an operating room (OR) drape 7, is lying on an examination table 5. A surgeon 3 is treating a region of the body 4 through an opening in the OR drape 7. The surgeon 3 holds a fluorescence scanner 1 in his hand, and with it, he can examine the body region to be treated.

The region 8 to be examined of the body 4 is shown schematically and enlarged. The body 4 may be covered, by the OR drape 7, except for an opening in the OR drape 7. The surgeon 3 aims the fluorescence scanner 1 centrally at the body region 8, which can be seen and reached through the opening.

Data detected by the fluorescence scanner 1 are typically transmitted in cordless fashion, to a personal computer (PC) workstation 9. The PC workstation 9 displays the data received, which are image data of the body region 8 to be examined, on a screen. The surgeon 3 can view the fluorescence scan on the screen of the PC workstation 9 and thus has the outcome of the scan immediately available for viewing. The surgeon can plan the surgical strategy or planning using the fluorescence scan, as needed.

To enable orientation to the image shown, the optical view of the fluorescence scan has a view of the same visible region or the same body region 8 superimposed thereon, in the form of a normal image obtained in the visible wavelength range. Based on the image in the visible wavelength range, the physician can recognize details of the body region 8 on the screen, and from the superimposed fluorescence scan, can associate the features shown on the scan with the visible points in the body region 8. Superimposition of an image made in the visible wavelength range permits the association with physical features even if the fluorescence is in a non-visible wavelength range, such as IR.

Figure 2:
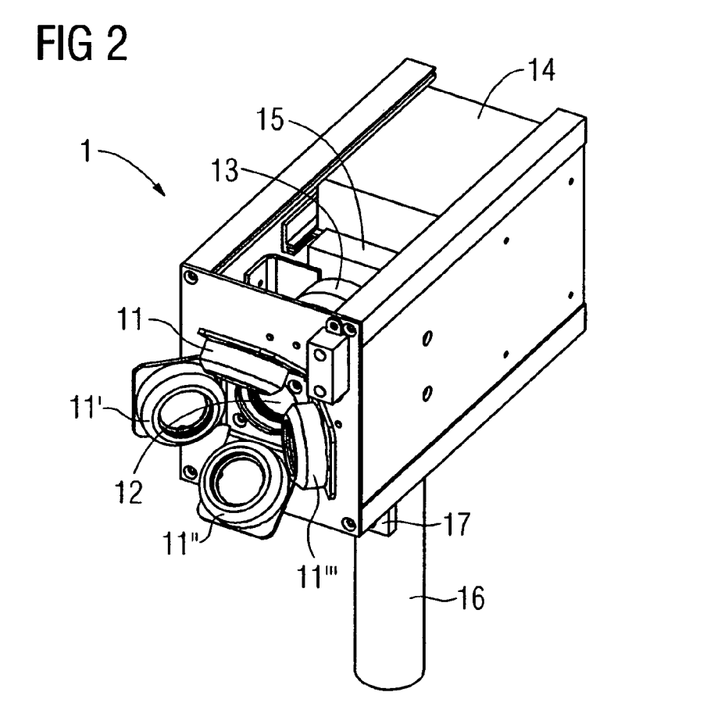
FIG. 2 is a perspective view of one embodiment of a fluorescence scanner with the outer housing open.

In FIG. 2, a fluorescence scanner 1 is shown in a perspective view. The upper covering of the housing has been omitted. The fluorescence scanner 1 has a handle 16 so that it can be manipulated by the surgeon. On the handle 16, there is a button 17, with which the physician can manually initiate a fluorescence scan.

In the front region, excitation light sources 11, 11', 11", 11''' are arranged such that they can illuminate a region at a distance of approximately 6 to 10 cm. For that purpose, they are arranged at an angle of approximately 45° to the front panel. This arrangement may correspond to a working distance where the scanning region should not be touched by the scanner, and on the other, excessively high excitation light intensity light sources may be avoided.

The excitation light sources 11, 11', 11", 11''' may be based on halogen light sources, and may be LEDs (light emitting diodes), laser diodes, and the like, depending on the wavelengths and intensities needed. Since an individual LED has a relatively low luminous intensity, LED arrays may be used for each light source. Each of the four LED arrays may have a luminous power of approximately 0.25 to 1 Watt.

A lens 12 is aimed frontally at the illuminated region, and by means of this lens a suitable pattern, such as a striped pattern or some other geometrical pattern, can be projected. The projection is done in a defined direction, or in other words at a defined angle relative to the fluorescence scanner 1. The pattern to be projected is generated by the pattern projector 13 and may pass through the lens 12, before it leaves the fluorescence scanner 1 in the direction of the body to be examined. Light that arrives from the body to be examined passes through the lens 12 and the pattern projector 13 and reaches a CCD camera 15. The CCD camera 15 is capable of recording images both in the wavelength range of visible light and in the wavelength range of the fluorescence. The image data recorded by the CCD camera 15 are received by a data acquisition unit 14 and transmitted to the outside, preferably in cordless fashion.

The data detected are processed further in a data processing system. The known projection pattern is projected onto the body 4 to be examined with distorted geometry, because of the angle between the pattern projection beam and the body 4 to be examined. The projection pattern may be recorded at a second geometric angle that differs from the first geometric angle of projection of the pattern. From the known angle, known pattern, and the observed distortion of the pattern in the optical image, the data processing system can calculate the 3D location information of each surface point on the body 4. This calculation of the 3D location information is based on geometric calculations. Hence, both a visible optical image and a 3D fluorescence image are obtained, which may be shown superimposed (fused) as a 3D fluorescence scan.

Figure 3:
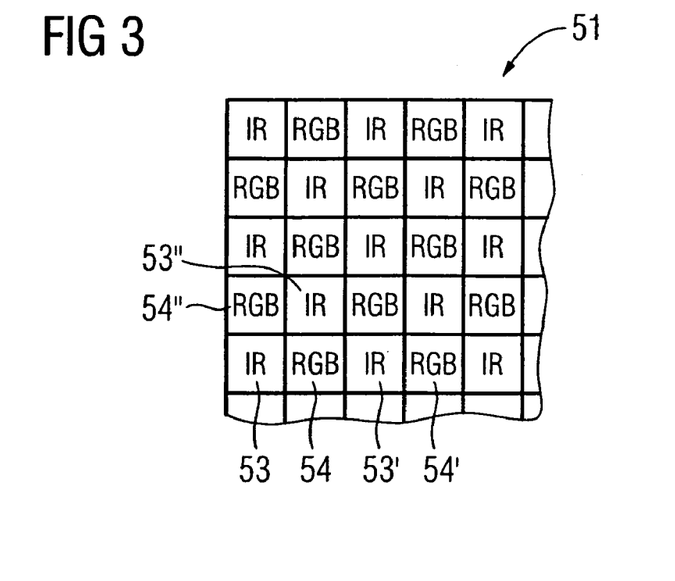
FIG. 3 is a schematic top view on an image sensor for recording both optical and fluorescence images in one embodiment.

FIG. 3 is an example of an image sensor of a CCD camera 15 that can be used in the fluorescence scanner 1 described above and is shown in a schematic top view. The surface of the image sensor is divided up into many approximately square surface portions 53, 54, 53', 54', . . . , which form a filter layer 51. Each of the adjacently located surface portions 53, 54, 53', 54', . . . have different filtering properties.

The surface portions 53, 53', 53", . . . are intended to allow light in the IR or NIR wavelength range to pass through, and are marked "IR" in the drawing. The filter characteristic of the surface portions 53, 53', 53", . . . does not allow or limits light in the wavelength range of visible light to pass through, as the IR or NIR fluorescent light would be washed out. Depending on the recording spectrum of the image detector located beneath the filter layer 51, which is not further visible in FIG. 3, not only visible light but also other wavelengths, may be filtered out. The surface portions 53, 53', 53", . . . pass IR optical energy and permit recording of fluorescence images.

The surface portions 54, 54', 54", . . . may allow light in the visible wavelength range to pass through. In accordance with a typical way of recording or displaying color images, visible light can be considered as being composed of red (R), yellow (G) and blue (B) components, and the surface portions are therefore marked "RGB" in the drawing. In an aspect, the RGB surface portions 54, 54', 54", . . . are formed by cutouts out of the filter layer 51; the presence of no filter material meets the requirement that visible light must be capable of passing through. In a further aspect, the portions are formed by a material which results in essentially no filtering. In still another aspect, RGB surface portions are formed by a material whose filter characteristic filters out light in the IR or NIR range. In this way, the visible light passed through can be prevented from being discolored by fluorescent light or its spectrum adulterated. The surface portions 54, 54', 54", ... thus pass visible light and permit the recording of a visible spectrum image.

The image sensor shown in FIG. 3 may record both an optical image and a fluorescence image simultaneously, each with half the resolution, compared with the highest possible resolution of the entire arrangement.

In another example of the fluorescence scanner 1, not shown, instead of the CCD camera 15 described above with a bifunctional filter layer 51, a CCD camera without such a filter layer 51 is provided. To enable recording with optical and fluorescence images with a conventional CCD camera, an additional filter is provided. The additional filter has a filter characteristic such that fluorescent light can pass through, while other light is filtered out or limited, so that the fluorescent light will not be washed out. In order nevertheless to still be capable of recording optical images, the filter can be moved out of the beam path, for example by means of a hinge mechanism or a displacement mechanism.

Figure 4:
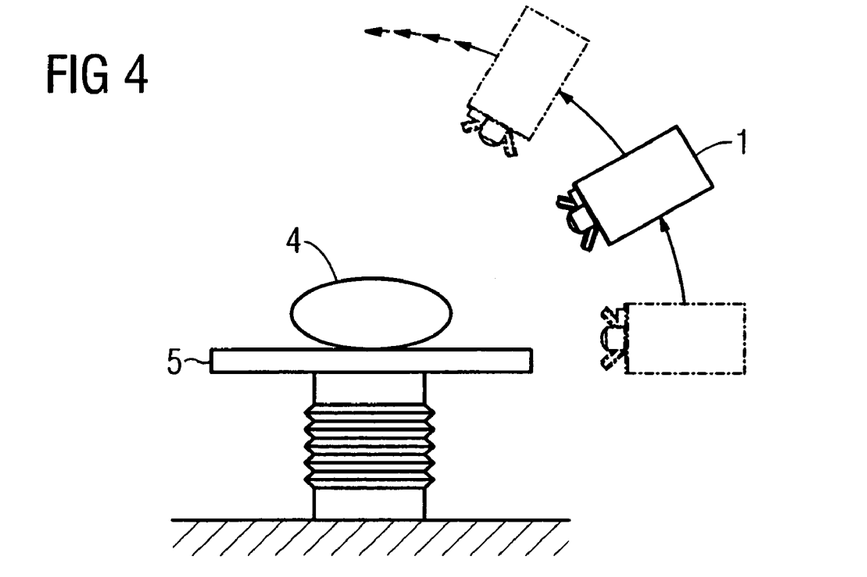
FIG. 4 is a schematic illustration of one embodiment of an incremental rotation of the fluorescence scanner.

In FIG. 4, a schematic illustration of an incremental rotation of the fluorescence scanner 1 about the body 4 to be examined is shown. The body 4 is supported on the examination table 5. Depending on the work environment, the examination table 5 can be a diagnosis table or an operating room table.

The fluorescence scanner 1 makes fluorescence scans of the body 4 from different angles of observation. The various angles of observation result from rotation about at least one axis, which in the variant shown is rotation about a horizontal axis perpendicular to the plane of view of the drawing. In the drawing, the rotary motion is represented by arc-shaped arrows. The fluorescence scanner 1 is shown in an orientation that is inclined slightly from the horizontal, but other possible orientations with a different inclination are also shown in dot-dashed lines.

The various angles of observation can be assumed manually, if a portable fluorescence scanner 1 of the kind explained in FIGS. 1 and 2 above is used. For that purpose, the surgeon makes fluorescence scans from angles of observation that appear appropriate to the surgeon, orienting the fluorescence scanner 1 by hand. The various angles of observation may, however, also be assumed automatically.

Figure 5:
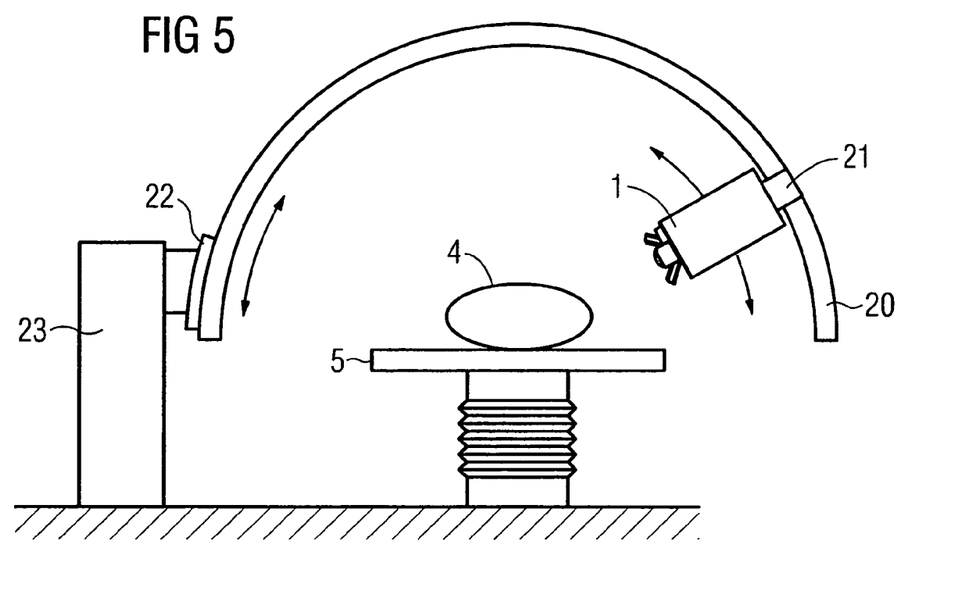
FIG. 5 is a schematic illustration of one embodiment of an apparatus for recording 3D fluorescence scans.

In FIG. 5, a schematic view of an apparatus for generating 3D fluorescence scans is shown. The apparatus includes a C arch 20 for rotatably supporting a fluorescence scanner 1. The fluorescence scanner 1 is supported in the C arch 20 by means of a carriage 21. The carriage 21 is supported displaceably in the C arch 20 so that the fluorescence scanner 1 may be rotated about the body 4 to be examined. The body 4 may be positioned on an examination table 5 approximately in the center of curvature of the C arch 20.

The C arch 20 is supported displaceably in a support 22, by way of which it is carried from a base station 23. Because of the additional displaceability of the C arch 20, the action radius of the apparatus is enhanced, compared to an arrangement with a rigidly supported C arch 20.

Both the C arch 20 and the carriage 21 may be automatically displaceable. To that end, the base station 23 includes a controller together with motor components, which however are not shown in the drawing. Via line connections, also not shown, inside the C arch 20, the power supply to the fluorescence scanner 1 is made, and both the recording control and the data connection can be implemented using the same kind of line connections, or by cordless techniques as are known in the art.

Figure 6:
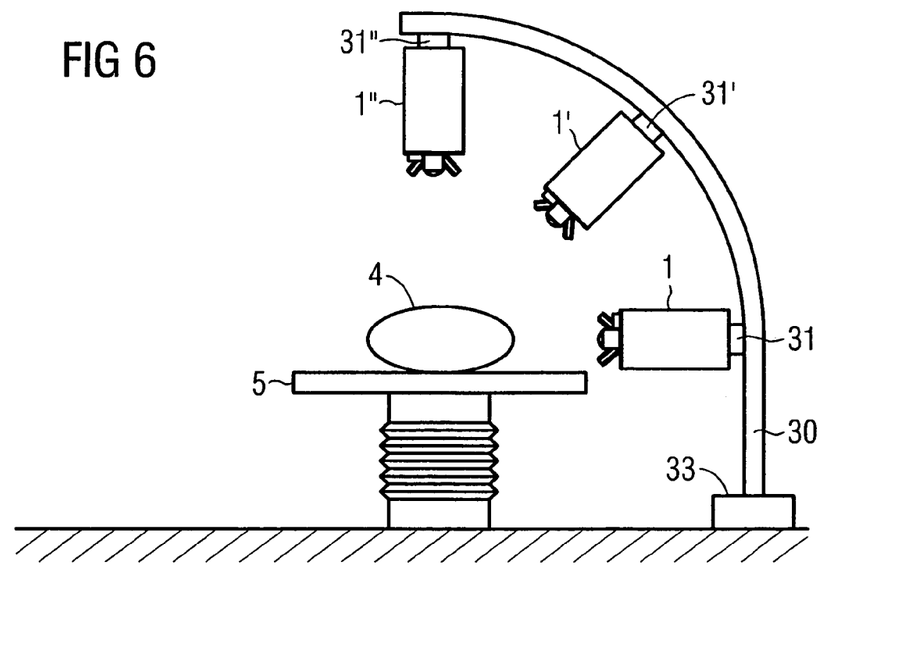
FIG. 6 is a schematic illustration of a further embodiment of an apparatus for recording 3D fluorescence scans.

FIG. 6 is a schematic view of a further apparatus for generating 3D fluorescence scans. The apparatus includes a rail 30 for the suspension of a plurality of fluorescence scanners 1, 1', 1". The rail 30 performs a similar function to the C arch 20 described above. However, the fluorescence scanners 1, 1', 1" are fixedly retained in the rail 30 via non-displaceable mounts 31, 31', 31". In this way, fluorescence scans can also be taken from different angles of observation, but the angles of observation are fixedly specified. On the one hand, this may make image processing easier, with the individual fluorescence scans joined together into one entire scan, since the observation geometry is known in advance. Furthermore, a complicated movement mechanism and movement controller maybe avoided. On the other hand, however, a plurality of fluorescence scanners 1, 1', 1" are used.

In this aspect, the rail 30 is supported in a base 33 standing on the floor. A certain spatial orientation is attained relative to the body 4 lying on the examination table 5. However, rails of another form and with a different support, for example on side walls or on the ceiling of the examining room, are also possible.

In another aspect, not shown, only one fluorescence scanner is provided, which is fixedly positioned. To enable making a number of scans from different angles of observation, the body to be examined is rotated, instead of the scanner. To that end, the body is supported on a positioning device, for example an examination table that is adjustable and rotatable for positioning purposes.

Figure 7:
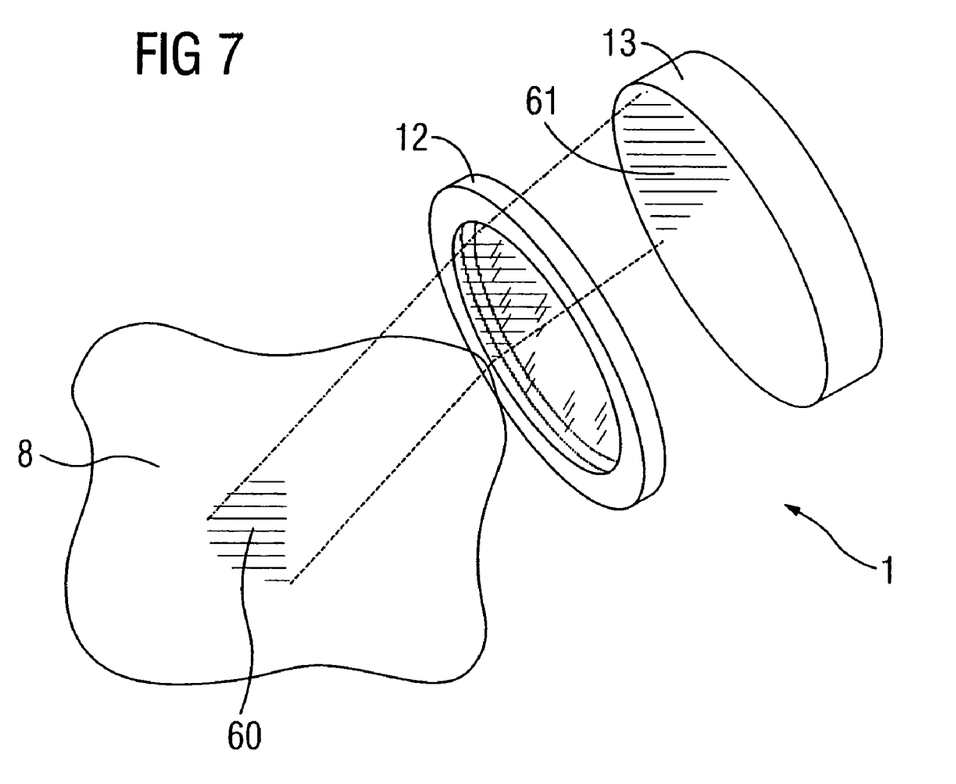
FIG. 7 is a schematic illustration of the pattern projector according to one embodiment.

FIG. 7 is a schematic view of the pattern projector 13. In the example shown, the pattern projector 13 projects a striped pattern 60; instead, however, some other pattern, typically a geometrical pattern, could be projected.

The pattern projector 13 has illuminants 61, which are arranged such that they are capable of projecting the pattern. In the variant shown with a striped pattern 60, the illuminants 61 may be disposed in stripes. The illuminants 61 can be LEDs or laser diodes, but halogen lamps or other technologies can be used.

The illuminants 61 are arranged such that light coming from the scanning region 8 of the body to be examined can reach the CCD camera 15, located behind the pattern projector 13, unhindered. For this reason, the illuminants 61 may be located not in but next to the beam path from the scanning region 8 to the CCD camera 15. Depending on the optical-geometrical arrangement, the illuminants 61 can also be located laterally, and their light can be deflected into the desired projection direction by means of one or more mirrors. As needed, the mirrors can either be located outside the beam path from the scanning region 8 to the CCD camera 15 or embodied as a semitransparent mirror, which does reflect the projection light but allows light from the scanning region 8 to the CCD camera 15 to pass through with as little hindrance as possible.

As a result, a series of individual 3D fluorescence scans of the same body 4 can be obtained. The scans may be joined together as needed by means of a data processing system into a panoramic view, so that a view of the entire body region being examined can be obtained. To facilitate joining them together, the individual scans are obtained mutually overlap at least in part. Based on the overlapping regions, the data processing system, using known registration methods or known scanner position, can adapt the various enlargements or reproduction scales of the individual scans, align their orientation with one another, and join the individual scans together seamlessly as one total scan.

Although only a few exemplary embodiments have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

The invention claimed is:

1. An optical scanner for producing a three dimensional fluorescence or luminescence scan, comprising:
   a pattern projector disposable to project an optical pattern onto an area; and
   an image detector configured to record a first image of the area in visible light, and a second image comprising at least one of a fluorescence or a luminescence of the area, wherein the optical pattern is suitable for computing a three dimensional surface profile of the area; and, the computed three dimensional surface profile of the area and the second image are superimposed for visual display.

2. The apparatus of claim 1, wherein the second image is recorded in visible light.

3. The apparatus of claim 1, wherein the area is illuminated in an optical wavelength region overlapping a fluorescence wavelength.

4. The apparatus of claim 1, wherein the area is illuminated in an optical wavelength substantially non-overlapping a fluorescence wavelength.

5. The apparatus of claim 1, wherein a first angle between the pattern projector and the area and a second angle between the image detector and the area are a same angle.

6. The apparatus of claim 5, wherein the optical path between the pattern projector and the area and the optical path between the image detector and the area are co-linear in the region between the optical imager and the area.

7. The apparatus of claim 1, further comprising a C-shaped arch having the pattern projector and the image detector displacably supported.

8. The apparatus of claim 7, further comprising:
   a data processing system configured to calculate 3D location information of a surface point of the area.

9. The apparatus as defined by claim 1, further comprising a rail on which a plurality of pattern projectors and image detectors are fixedly supported.

10. The apparatus of claim 1, further comprising:
    a data processing system configured to calculate 3D location information of a surface point of the area.

11. The apparatus of claim 1, wherein a first first image and a second first image of the area are obtained by rotating the apparatus incrementally about at one axis of an object to be examined, where a first angle of at least one of the pattern projector or the image detector has changed with respect to the area.

12. A method for recording a 3D fluorescence and/or luminescence scan, the method comprising:
    projecting a pattern onto a surface of a first region;
    recording a first optical image of the pattern projected onto the surface of the first region from a direction which is at a predetermined angle to the direction of the projection of the pattern;
    recording at least one of a fluorescence or a luminescence image of the surface of the first region;
    calculating 3D location information of surface of the first region from the recorded first optical image of the projected pattern;
    superimposing the computed 3D location information on at least one of the fluorescence image or the luminescence image; and displaying the superimposed image.

13. The method as defined by claim 12, further comprising:
    repeating the steps of projecting the pattern, recording the optical image, and recording at least one of the fluorescence or luminescence image of a second region at a different angle of observation, wherein the first region at least partially overlaps the second region; and
    joining together the individual 3D fluorescence and/or luminescence scans representing a first region and a second region to form a composite image.

14. The method of claim 13, where the predetermined angle is zero.

15. The method of claim 12, wherein the pattern is a geometric pattern.

* * * * *